United States Patent
Yachnis et al.

(10) Patent No.: US 12,186,528 B2
(45) Date of Patent: Jan. 7, 2025

(54) INFUSION PUMP CASSETTE LATCH

(71) Applicant: EITAN MEDICAL LTD., Netanya (IL)

(72) Inventors: Michael Yachnis, Netanya (IL); Amir Rasowsky, Yakir (IL); Gidi Pesach, Kfar Vitkin (IL)

(73) Assignee: EITAN MEDICAL LTD., Netanya (IL)

( * ) Notice: Subject to any disclaimer, the term of this patent is extended or adjusted under 35 U.S.C. 154(b) by 807 days.

(21) Appl. No.: 17/433,439

(22) PCT Filed: Mar. 4, 2020

(86) PCT No.: PCT/IL2020/050247
§ 371 (c)(1),
(2) Date: Aug. 24, 2021

(87) PCT Pub. No.: WO2020/178825
PCT Pub. Date: Sep. 10, 2020

(65) Prior Publication Data
US 2022/0040403 A1 Feb. 10, 2022

Related U.S. Application Data

(60) Provisional application No. 62/814,001, filed on Mar. 5, 2019.

(51) Int. Cl.
*A61M 5/142* (2006.01)
*A61M 5/14* (2006.01)
(Continued)

(52) U.S. Cl.
CPC .......... *A61M 5/142* (2013.01); *A61M 5/1413* (2013.01); *A61M 2205/12* (2013.01);
(Continued)

(58) Field of Classification Search
CPC .. A61M 2005/14573; A61M 2205/121; A61M 5/1413; A61M 5/142; A61M 39/28;
(Continued)

(56) References Cited

U.S. PATENT DOCUMENTS

| | | |
|---|---|---|
| 3,379,950 A | 4/1968 | Friedline |
| 4,236,880 A | 12/1980 | Archibald |
| (Continued) | | |

FOREIGN PATENT DOCUMENTS

| | | |
|---|---|---|
| CN | 103727021 | 4/2014 |
| EP | 0182502 | 5/1986 |
| (Continued) | | |

OTHER PUBLICATIONS

An Office Action dated Nov. 17, 2023, which issued during the prosecution of U.S. Appl. No. 16/967,952, 53pp.
(Continued)

*Primary Examiner* — Nathan R Price
*Assistant Examiner* — Amina Ishrat
(74) *Attorney, Agent, or Firm* — The Roy Gross Law Firm, LLC; Roy Gross (57) ABSTRACT

A tube cassette (22) for receiving infusion tubing is shaped to define a locking surface (26). A pump (20) includes a latch (28) which engages with the locking surface and locks the cassette in a preset position with respect to the pump. A mechanical stop (38) in the pump stops motion of the cassette in a first direction, such that the cassette has moved past the preset position. Until motion of the cassette is stopped by the mechanical stop, the latch allows motion of the cassette past the preset position in the first direction. The latch automatically moves from an open position to a cassette-withdrawal-inhibiting position upon engagement of the latch with the locking surface, and subsequently locks the cassette in the preset position by pushing the cassette in a second direction, from past the preset position to the preset position. Other applications are also described.

11 Claims, 5 Drawing Sheets

(51) Int. Cl.
  *F04B 43/12* (2006.01)
  *F04B 53/16* (2006.01)
  *F04B 53/22* (2006.01)
(52) U.S. Cl.
  CPC ........ *A61M 2205/121* (2013.01); *F04B 43/12* (2013.01); *F04B 43/1284* (2013.01); *F04B 53/16* (2013.01); *F04B 53/22* (2013.01)
(58) Field of Classification Search
  CPC ............ A61M 39/284; A61M 2205/12; A61M 2205/6045; F04B 39/00; F04B 39/12; F04B 39/121; F04B 39/14; F04B 53/16; F04B 53/22; F04B 43/1284
  See application file for complete search history.

(56) References Cited

U.S. PATENT DOCUMENTS

| | | |
|---|---|---|
| 4,314,567 A | 2/1982 | Cannon |
| 4,322,668 A | 3/1982 | Trussler et al. |
| 4,391,600 A | 7/1983 | Archibald |
| 4,650,469 A | 3/1987 | Berg et al. |
| 4,735,558 A | 4/1988 | Kienholz et al. |
| 5,018,945 A | 5/1991 | D'Silva |
| 5,049,047 A | 9/1991 | Polaschegg et al. |
| 5,096,385 A | 3/1992 | Georgi et al. |
| 5,116,203 A | 5/1992 | Natwick et al. |
| 5,340,951 A | 8/1994 | Hungerbuhler et al. |
| 5,437,642 A | 8/1995 | Thill et al. |
| 5,567,119 A | 10/1996 | Johnson et al. |
| 5,755,691 A | 5/1998 | Hilborne |
| 5,807,075 A | 9/1998 | Jacobsen et al. |
| 5,807,322 A | 9/1998 | Lindsey et al. |
| 5,843,035 A | 12/1998 | Bowman et al. |
| 5,954,485 A | 9/1999 | Johnson et al. |
| 6,231,320 B1 | 5/2001 | Lawless et al. |
| 6,312,227 B1 | 11/2001 | Davis |
| 6,494,864 B1 | 12/2002 | Kerwin et al. |
| 6,523,414 B1 | 2/2003 | Malmstrom et al. |
| 6,531,708 B1 | 3/2003 | Malmstrom et al. |
| 6,554,806 B2 | 4/2003 | Butterfield et al. |
| 6,659,976 B2 | 12/2003 | Beck et al. |
| 6,679,862 B2 | 1/2004 | Diaz et al. |
| 6,702,779 B2 | 3/2004 | Connelly et al. |
| 6,750,468 B2 | 6/2004 | Malmstrom et al. |
| 6,852,094 B2 | 2/2005 | Beck et al. |
| 6,889,556 B2 | 5/2005 | Steger |
| 6,907,788 B2 | 6/2005 | Malmstrom et al. |
| 6,908,452 B2 | 6/2005 | Diaz et al. |
| 6,979,311 B2 | 12/2005 | Miles et al. |
| 7,048,715 B2 | 5/2006 | Diaz et al. |
| 7,059,840 B2 | 6/2006 | Corwin et al. |
| 7,070,575 B2 | 7/2006 | Beck et al. |
| 7,092,796 B2 | 8/2006 | Vanderveen |
| 7,121,143 B2 | 10/2006 | Malmstrom et al. |
| 7,163,381 B1 | 1/2007 | Barak |
| 7,356,382 B2 | 4/2008 | Vanderveen |
| 7,384,408 B2 | 6/2008 | Barak |
| 7,497,842 B2 | 3/2009 | Diaz et al. |
| 7,695,448 B2 | 4/2010 | Cassidy et al. |
| 7,726,174 B2 | 6/2010 | Riley et al. |
| 7,758,551 B2 | 7/2010 | Wiesner et al. |
| 7,819,838 B2 | 10/2010 | Ziegler et al. |
| 7,875,004 B2 | 1/2011 | Yodfat et al. |
| 7,881,883 B2 | 2/2011 | Remde |
| 7,892,199 B2 | 2/2011 | Mhatre et al. |
| 7,896,197 B2 | 3/2011 | Furey et al. |
| 7,921,718 B2 | 4/2011 | Malmstrom et al. |
| 7,922,700 B2 | 4/2011 | Evans et al. |
| 7,967,773 B2 | 6/2011 | Amborn et al. |
| 7,981,082 B2 | 7/2011 | Wang et al. |
| 8,025,654 B2 | 9/2011 | Barak |
| 8,034,020 B2 | 10/2011 | Dewey |
| 8,048,022 B2 | 11/2011 | Moy et al. |
| 8,081,069 B2 | 12/2011 | Haueter et al. |
| 8,105,269 B2 | 1/2012 | Zhou |
| 8,142,400 B2 | 3/2012 | Rotem et al. |
| 8,152,780 B2 | 4/2012 | Evans et al. |
| 8,167,832 B2 | 5/2012 | Bowman et al. |
| 8,182,461 B2 | 5/2012 | Pope et al. |
| 8,225,639 B2 | 7/2012 | Riley et al. |
| 8,232,484 B2 | 7/2012 | Hauck |
| 8,286,505 B2 | 10/2012 | Wade |
| 8,287,495 B2 | 10/2012 | Michaud et al. |
| 8,298,184 B2 | 10/2012 | Diperna et al. |
| 8,328,786 B2 | 12/2012 | Strickler et al. |
| 8,343,111 B2 | 1/2013 | Beck et al. |
| 8,361,021 B2 | 1/2013 | Wang et al. |
| 8,378,837 B2 | 2/2013 | Wang et al. |
| 8,394,051 B2 | 3/2013 | Geipel |
| 8,419,676 B2 | 4/2013 | Evans et al. |
| 8,448,523 B2 | 5/2013 | Richter |
| 8,486,005 B2 | 7/2013 | Yodfat et al. |
| 8,486,020 B2 | 7/2013 | Hills et al. |
| 8,496,613 B2 | 7/2013 | Zhou |
| 8,539,672 B2 | 9/2013 | Eggers et al. |
| 8,567,235 B2 | 10/2013 | Bojan et al. |
| 8,641,671 B2 | 2/2014 | Michaud et al. |
| 8,657,778 B2 | 2/2014 | Ziegler et al. |
| 8,690,014 B2 | 4/2014 | Haueter et al. |
| 8,690,860 B2 | 4/2014 | Abal |
| 8,733,178 B2 | 5/2014 | Bivans et al. |
| 8,752,436 B2 | 6/2014 | Beck et al. |
| 8,758,323 B2 | 6/2014 | Michaud et al. |
| 8,771,227 B2 | 7/2014 | Connelly et al. |
| 8,795,225 B2 | 8/2014 | Lewis et al. |
| 8,808,230 B2 | 8/2014 | Rotstein |
| 8,821,432 B2 | 9/2014 | Unverdorben |
| 8,852,141 B2 | 10/2014 | Mhatre et al. |
| 8,859,972 B2 | 10/2014 | Cummings et al. |
| 8,876,787 B2 | 11/2014 | Beck et al. |
| 8,900,213 B2 | 12/2014 | Pope et al. |
| 8,926,561 B2 | 1/2015 | Verhoef et al. |
| 8,943,894 B2 | 2/2015 | Geipel |
| 8,945,064 B2 | 2/2015 | Gravesen et al. |
| 8,961,453 B2 | 2/2015 | Bowman et al. |
| 8,974,415 B2 | 3/2015 | Robert et al. |
| 8,986,252 B2 | 3/2015 | Cummings et al. |
| 8,986,253 B2 | 3/2015 | Diperna |
| 9,004,886 B2 | 4/2015 | Beck et al. |
| 9,005,153 B2 | 4/2015 | Kopperschmidt et al. |
| 9,017,296 B2 | 4/2015 | Beck et al. |
| 9,033,923 B2 | 5/2015 | Hartman et al. |
| 9,101,712 B2 | 8/2015 | Denis et al. |
| 9,109,966 B2 | 8/2015 | Duits |
| 9,132,230 B2 | 9/2015 | Blomquist |
| 9,162,023 B2 | 10/2015 | Barnes et al. |
| 9,173,998 B2 | 11/2015 | Rosinko et al. |
| 9,211,377 B2 | 12/2015 | Diperna et al. |
| 9,227,008 B2 | 1/2016 | Magnenat et al. |
| 9,234,850 B2 | 1/2016 | Hammond et al. |
| 9,248,230 B2 | 2/2016 | Geipel et al. |
| 9,272,087 B2 | 3/2016 | Halbert et al. |
| 9,285,324 B2 | 3/2016 | Leuenberger Jockel |
| 9,308,323 B2 | 4/2016 | Adams |
| 9,375,531 B1 | 6/2016 | Lee et al. |
| 9,408,968 B2 | 8/2016 | Browne et al. |
| 9,415,158 B2 | 8/2016 | Miller et al. |
| 9,427,521 B2 | 8/2016 | Pope et al. |
| 9,468,713 B2 | 10/2016 | Hoenninger, III et al. |
| 9,474,854 B2 | 10/2016 | Mhatre et al. |
| 9,480,793 B2 | 11/2016 | Mhatre et al. |
| 9,480,794 B2 | 11/2016 | Keith et al. |
| 9,545,478 B2 | 1/2017 | Abal |
| 9,561,323 B2 | 2/2017 | Plahey et al. |
| 9,603,998 B2 | 3/2017 | Geipel et al. |
| 9,610,404 B2 | 4/2017 | Rotstein |
| 9,642,777 B2 | 5/2017 | Lewis et al. |
| 9,662,437 B2 | 5/2017 | Moosai |
| 9,675,756 B2 | 6/2017 | Kamen et al. |
| 9,677,555 B2 | 6/2017 | Kamen et al. |
| 9,682,192 B2 | 6/2017 | Marsh et al. |
| 9,683,562 B2 | 6/2017 | Davis et al. |
| 9,717,849 B2 | 8/2017 | Mhatre et al. |

(56) References Cited

U.S. PATENT DOCUMENTS

| | | |
|---|---|---|
| 9,757,517 B2 | 9/2017 | Eberhard |
| 9,770,552 B2 | 9/2017 | Hartman et al. |
| 9,775,947 B2 | 10/2017 | Keith et al. |
| 9,789,251 B2 | 10/2017 | Robert et al. |
| 9,839,744 B2 | 12/2017 | Muto et al. |
| 9,879,668 B2 | 1/2018 | Yavorsky et al. |
| 9,901,676 B2 | 2/2018 | Mijers et al. |
| 9,932,977 B2 | 4/2018 | Bresina et al. |
| 9,937,290 B2 | 4/2018 | Connelly et al. |
| 9,937,291 B2 | 4/2018 | Eberhard |
| 9,958,344 B2 | 5/2018 | Burkhard |
| 9,962,486 B2 | 5/2018 | Rosinko et al. |
| 9,987,424 B2 | 6/2018 | Kim |
| 9,995,642 B2 | 6/2018 | Shimoyama et al. |
| 10,004,847 B2 | 6/2018 | Wander et al. |
| 10,006,453 B2 | 6/2018 | Girard et al. |
| 10,022,494 B2 | 7/2018 | Shimizu |
| 10,022,495 B2 | 7/2018 | Halbert et al. |
| 10,022,496 B2 | 7/2018 | Geipel et al. |
| 10,046,112 B2 | 8/2018 | Oruklu et al. |
| 10,080,836 B2 | 9/2018 | Juretich et al. |
| 10,092,697 B2 | 10/2018 | Nessel et al. |
| 10,112,009 B2 | 10/2018 | Dudar et al. |
| 10,151,646 B2 | 12/2018 | Heo et al. |
| 10,539,453 B2 | 1/2020 | Hauck |
| 11,213,460 B2 | 1/2022 | O'Keefe et al. |
| 2003/0141468 A1 | 7/2003 | Malmstrom et al. |
| 2005/0107923 A1 | 5/2005 | Vanderveen |
| 2006/0173412 A1 | 8/2006 | Susi |
| 2006/0189926 A1 | 8/2006 | Hall et al. |
| 2006/0206054 A1 | 9/2006 | Shekalim |
| 2006/0229531 A1 | 10/2006 | Goldberger et al. |
| 2007/0123781 A1 | 5/2007 | Callahan et al. |
| 2007/0179435 A1 | 8/2007 | Braig et al. |
| 2008/0283296 A1 | 11/2008 | Zamora et al. |
| 2009/0221964 A1 | 9/2009 | Rotem et al. |
| 2009/0240201 A1 | 9/2009 | Rotem et al. |
| 2009/0293588 A1 | 12/2009 | Riley et al. |
| 2010/0106082 A1 | 4/2010 | Zhou |
| 2010/0114001 A1 | 5/2010 | O'Mahony |
| 2010/0212407 A1 | 8/2010 | Stringham et al. |
| 2010/0280446 A1 | 11/2010 | Kalpin |
| 2011/0087165 A1 | 4/2011 | Amborn et al. |
| 2011/0152772 A1 | 6/2011 | Rotem et al. |
| 2011/0190606 A1 | 8/2011 | Gable et al. |
| 2012/0205312 A1 | 8/2012 | Hogard |
| 2012/0238949 A1 | 9/2012 | Kalpin |
| 2012/0330574 A1 | 12/2012 | Ruiter et al. |
| 2013/0035659 A1 | 2/2013 | Hungerford et al. |
| 2013/0226129 A1 | 8/2013 | Unverdorben |
| 2013/0336814 A1 | 12/2013 | Kamen et al. |
| 2014/0066850 A1 | 3/2014 | Robert et al. |
| 2014/0119954 A1 | 5/2014 | Schweitzer et al. |
| 2014/0121639 A1 | 5/2014 | Lowery et al. |
| 2014/0228755 A1 | 8/2014 | Darrah et al. |
| 2015/0238689 A1 | 8/2015 | Shimizu |
| 2015/0367120 A1 | 12/2015 | Kusters et al. |
| 2018/0140770 A1 | 5/2018 | Hetchler et al. |
| 2018/0200456 A1 | 7/2018 | Eitan et al. |
| 2018/0318505 A1 | 11/2018 | Eitan et al. |
| 2020/0085695 A1 | 3/2020 | O'Keefe et al. |
| 2020/0282138 A1 | 9/2020 | Eitan et al. |
| 2021/0178062 A1 | 6/2021 | Eitan |
| 2021/0212903 A1 | 7/2021 | O'Keefe et al. |
| 2021/0353507 A1 | 11/2021 | O'Keefe et al. |

FOREIGN PATENT DOCUMENTS

| | | |
|---|---|---|
| EP | 1381843 | 3/2009 |
| EP | 2040056 | 9/2010 |
| EP | 1381889 | 3/2016 |
| EP | 2570826 | 8/2016 |
| EP | 3834862 | 6/2021 |
| FR | 2553151 | 4/1985 |
| GB | 2150644 | 7/1985 |
| WO | 02/068018 | 9/2002 |
| WO | 2012/126744 | 9/2012 |
| WO | 2019/155453 | 8/2019 |
| WO | 2020060996 A1 | 3/2020 |
| WO | 2020/178824 | 9/2020 |
| WO | 2021146374 A1 | 7/2021 |

OTHER PUBLICATIONS

An Office Action dated Sep. 30, 2019, which issued during the prosecution of U.S. Appl. No. 15/740,365.

European Search Report dated Jun. 21, 2019 which issued during the prosecution of European Application No. 16817348.2.

An International Search Report and a Written Opinion both dated Aug. 5, 2018, which issued during the prosecution of Applicant's PCT/IL2018/050409.

An Office Action dated Jun. 22, 2020, which issued during the prosecution of U.S. Appl. No. 15/740,365.

European Search Report dated Jun. 4, 2020, which issued during the prosecution of Applicant's European App No. 20160966.6.

European Search Report dated May 12, 2021 which issued during the prosecution of Applicant's European App No. 20212979.7.

An International Search Report and a Written Opinion both dated May 15, 2020, which issued during the prosecution of Applicant's PCT/IL2020/050249.

An International Search Report and a Written Opinion both dated Jun. 17, 2020, which issued during the prosecution of Applicant's PCT/IL2020/050247.

Notice of Allowance dated Aug. 4, 2021, which issued during the prosecution of U.S. Appl. No. 16/808,652.

U.S. Appl. No. 62/814,001, filed Mar. 5, 2019.

European Search Report dated Oct. 8, 2021 which issued during the prosecution of Applicant's European App No. 18905766.4.

INFUSION PUMP CASSETTE LATCH

CROSS-REFERENCE TO RELATED APPLICATIONS

The present application is the US national stage application of PCT/IL2020/050247, filed Mar. 4, 2020, which published as PCT Publication WO 2020/178825 to Yachnis, and which claims the priority of U.S. 62/814,001 to Yachnis et al., filed Mar. 5, 2019 entitled, "Infusion pump cassette latch," which is incorporated herein by reference.

FIELD OF THE INVENTION

The present invention relates generally to medical fluid-delivery devices, and more specifically to infusion pumps.

BACKGROUND

Pumps are often used in the medical industry for delivering fluids, e.g., drugs, or diagnostic fluids, to subjects. One type of medical pump is an infusion pump, used to infuse a fluid into a subject's circulatory system via infusion tubing. Some infusion pumps include a valve, or system of valves, that may occlude flow within the infusion tubing by pressing on the outside of the fluid-filled infusion tubing. Often infusion pumps engage with the infusion tubing via a tube cassette.

SUMMARY OF THE INVENTION

Infusion pumps often engage with infusion tubing via a tube cassette that receives the infusion tubing and is subsequently coupled to the infusion pump. The following are some properties and phenomena that may occur in infusion pumps that utilize tube cassettes:
- In some infusion pumps, the tube cassette has to be inserted in a particular way, e.g., starting from a particular side of the pump and pivoting down towards the opposite side of the pump.
- In some infusion pumps, the coupling of the tube cassette and the pump may have a region of meta-stability, at which in the absence of any force external to the tube cassette, the tube cassette may be engaged with the pump but in an unstable manner, whereby the tube cassette may pop out at any point.
- In some infusion pumps, during delivery of the fluid to the subject, if an external force is applied to the tube cassette, pressure may be put on the infusion tubing causing either a bolus delivery to the patient, or inaccuracy of the delivery volume.

In light of these considerations, an infusion pump and tube cassette are provided, in accordance with some applications of the present invention. The tube cassette receives the infusion tubing and is removably couplable to the pump. The pump and tube cassette have a locking system that includes a locking surface on the tube cassette, a latch on the pump, and a mechanical stop disposed within the pump. When the tube cassette is coupled to the pump, the latch lockingly engages with the locking surface in such a way as to ensure that, upon full insertion of the tube cassette into the pump, the latch (a) automatically moves to a cassette-withdrawal-inhibiting position, avoiding a possibly meta-stable connection between the tube cassette and the pump, and (b) locks the tube cassette in a preset position with respect to the pump.

As the tube cassette is inserted into the pump, motion of the tube cassette in a first direction, toward the pump, can continue all the way until the tube cassette is stopped by the mechanical stop. The mechanical stop is positioned to stop the motion of the tube cassette once the tube cassette has "over-traveled," i.e., has moved past the preset position. The "over-travel" of the tube cassette ensures that the latch fully engages the locking surface, without the latch potentially getting stuck in a meta-stable position. After the latch has achieved a state of making sure the cassette cannot fall out of the pump, the latch then locks the tube cassette in the preset position by pushing the tube cassette back from past the preset position (where it was stopped by the mechanical stop) to the preset position.

There is therefore provided, in accordance with some applications of the present invention, apparatus for delivering a fluid to a subject through infusion tubing, the apparatus including:
(A) a tube cassette configured to receive the infusion tubing, the tube cassette shaped to define a locking surface;
(B) a pump including a latch,
 (i) the tube cassette being configured to be removably coupled to the pump, and
 (ii) the latch being configured to (a) engage with the locking surface and (b) lock the tube cassette in a preset position with respect to the pump when the tube cassette is coupled to the pump; and
(C) a mechanical stop disposed within the pump,
 (i) the mechanical stop being positioned to stop motion of the tube cassette in a first direction, such that when the motion of the tube cassette in the first direction is stopped by the mechanical stop, the tube cassette has moved past the preset position in the first direction, and
 (ii) the latch being configured to:
  (a) until the motion of the tube cassette is stopped by the mechanical stop, allow motion of the tube cassette past the preset position in the first direction,
  (b) automatically move from an open position to a cassette-withdrawal-inhibiting position upon engagement of the latch with the locking surface, and
  (c) subsequently, lock the tube cassette in the preset position by pushing the tube cassette in a second direction opposite the first direction, from past the preset position to the preset position.

For some applications, the latch is a spring-loaded latch.
For some applications, the latch is configured to, during the coupling of the tube cassette to the pump, sequentially:
(a) rotate in a first rotational direction during a transition from (i) an initial position prior to the tube cassette being coupled to the pump to (ii) the open position, during motion of the tube cassette in the first direction,
(b) rotate in a second rotational direction, opposite the first rotational direction, in the transition from (i) the open position to (ii) the cassette-withdrawal-inhibiting position, and
(c) continue rotation in the second rotational direction during the pushing of the tube cassette in the second direction from past the preset position to the preset position, such that the latch returns to the initial position subsequently to the pushing of the tube cassette in the second direction.

For some applications, the cassette-withdrawal-inhibiting position of the latch is between (a) an initial position of the latch prior to the tube cassette being coupled to the pump and (b) the open position.

For some applications, the pump and the tube cassette are configured such that, in the absence of a sufficient external force maintaining the motion of the tube cassette in the first direction prior to the engagement of the latch with the locking surface, the pump is configured to eject the tube cassette by pushing the infusion tubing which in turn pushes the tube cassette from the pump.

For some applications, the latch includes a lower latch surface, the lower latch surface being configured to engage with the locking surface of the tube cassette, the lower locking surface having a radius of curvature that is substantially equal to a distance between an axis of rotation of the latch and the lower latch surface.

For some applications:
the locking surface is a lower locking surface, and the tube cassette is further shaped to define an upper locking surface, opposite the lower locking surface, and
the latch includes a lower latch surface and an upper latch surface, (a) the lower latch surface being configured to engage with the lower locking surface, and (b) the upper latch surface being configured to engage with the upper locking surface when the tube cassette is coupled to the pump, such that:
(i) engagement between the lower latch surface and the lower locking surface inhibits cassette withdrawal when the latch moves from the open position to the cassette-withdrawal-inhibiting position, and
(ii) subsequently, the upper latch surface pushes the tube cassette in the second direction by pushing on the upper locking surface of the tube cassette.

For some applications, the lower and upper latch surfaces are shaped to define the preset position of the tube cassette, such that subsequently to the upper latch surface pushing the tube cassette in the second direction, (a) movement of the tube cassette in the first direction is inhibited by the upper latch surface, and (b) movement of the tube cassette in the second direction is inhibited by the lower latch surface.

For some applications, the lower locking surface is shaped to define a radius of curvature that is substantially equal to a distance between an axis of rotation of the latch and the lower latch surface.

For some applications:
the locking surface is a first locking surface and the tube cassette is shaped to define a second locking surface, and
the latch is a first latch and the pump further includes a second latch, the second latch being configured to (a) lockingly engage with the second locking surface and (b) lock the tube cassette in the preset position with respect to the pump when the tube cassette is coupled to the pump.

For some applications, the first and second latches are disposed on opposite sides of the pump.

The present invention will be more fully understood from the following detailed description of applications thereof, taken together with the drawings, in which:

DETAILED DESCRIPTION

Figure 1A:
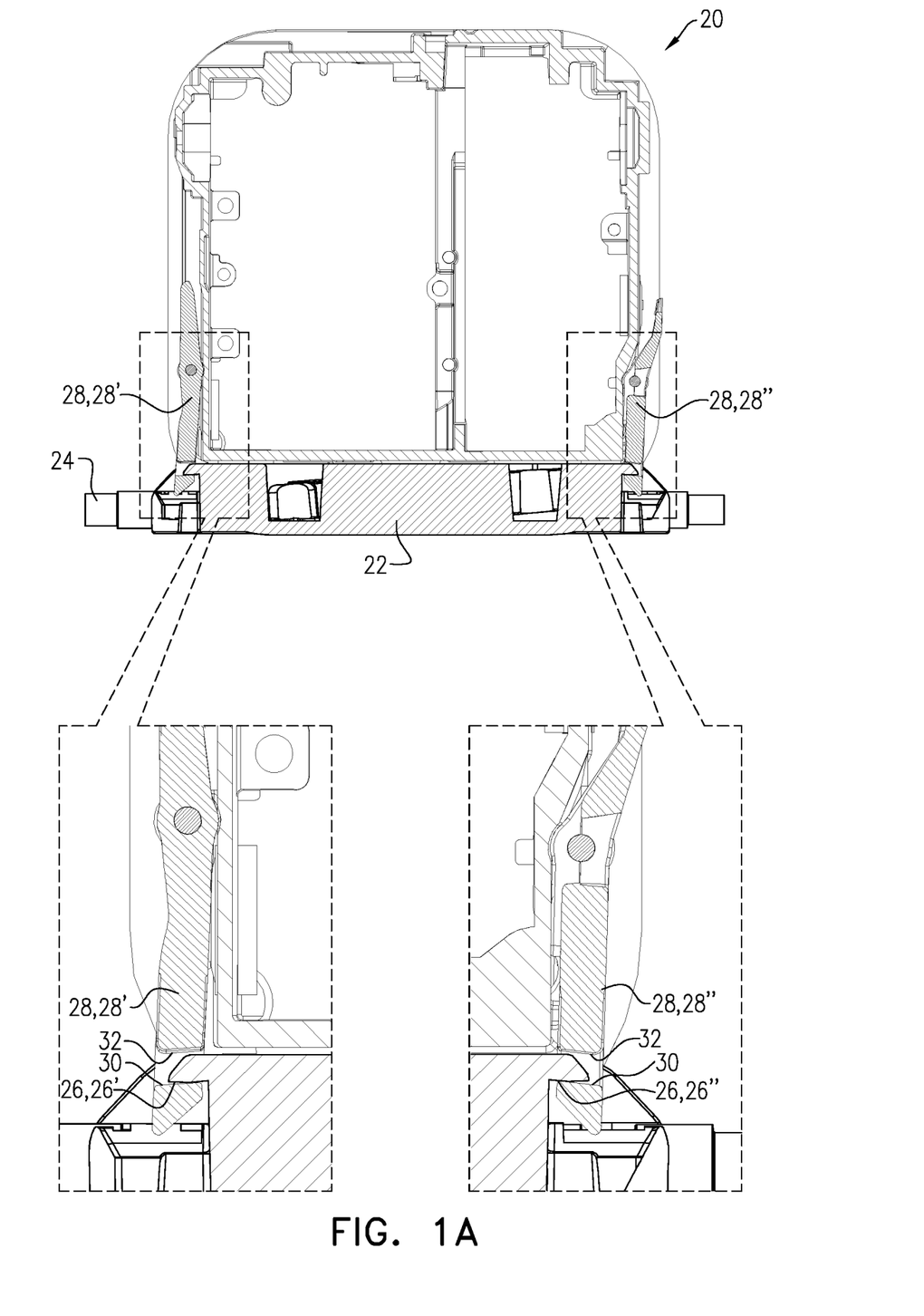
FIG. 1A is a schematic illustration of a pump with a tube cassette coupled to the pump, in accordance with some applications of the present invention.

Reference is now made to FIG. 1A, which is a schematic illustration of a pump 20 with a tube cassette 22 coupled to the pump, in accordance with some applications of the present invention. Pump 20 is typically an infusion pump, e.g., a volumetric infusion pump, or a peristaltic infusion pump, that delivers fluid, e.g., drugs or diagnostic fluids, to subjects through infusion tubing 24. Tube cassette 22 receives infusion tubing 24 and is removably couplable to pump 20, such that pump 20 engages with infusion tubing 24 via tube cassette 22.

Typically, tube cassette 22 is shaped to define at least one locking surface 26, e.g., a first locking surface 26' and a second locking surface 26" respectively on either side of tube cassette 22. Typically, pump 20 comprises at least one latch 28, e.g., a first latch 28' and a second latch 28" disposed respectively on either side of pump 20. As tube cassette 22 is coupled to pump 20, e.g., inserted into pump 20 by being pushed into pump 20 in a first direction toward pump 20, latch 28 lockingly engages a locking surface 26 of tube cassette 22. Typically, such as is shown in FIG. 1A, first latch 28' engages with first locking surface 26' and second latch 28" engages with second locking surface 26".

Subsequently to the latch 28 engaging with locking surface 26, latch 28 (e.g., latches 28' and 28") locks tube cassette 22 in a preset position with respect to pump 20, as further described hereinbelow with reference to FIGS. 2 and 3. FIG. 1A shows tube cassette 22 already locked in the preset position after having been coupled to pump 20. For some applications, as further described hereinbelow, each latch 28 has a lower latch surface 30 and an upper latch surface 32.

Figure 1B:
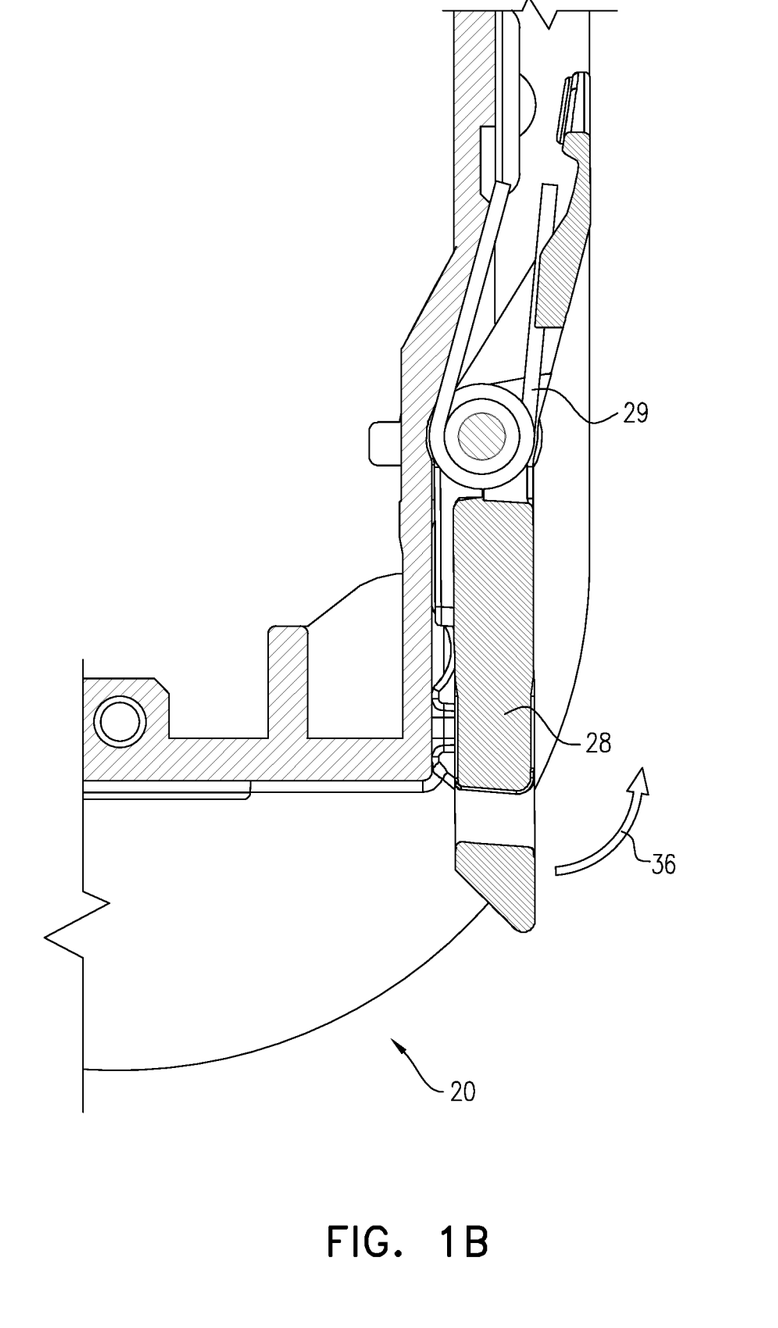
FIG. 1B is a schematic illustration of a latch of the pump, in accordance with some applications of the present invention.

Reference is now made to FIG. 1B, which is a schematic illustration of latch 28, in accordance with some applications of the present invention. For some applications, latches 28 are spring-loaded latches. As further described hereinbelow, tube cassette 22 is coupled to pump 20 typically by a user pushing tube cassette 22 into pump 20. In turn, tube cassette 22 pushes latch to rotate, in a first rotational direction, represented by curved arrow 36. Spring 29 spring-loads latch 28, such that as latch 28 rotates in the first rotational direction, spring 29 biases latch 28 to return to its initial position by rotating in a second rotational direction, opposite the first rotational direction (represented by curved arrows 42 in FIGS. 2 and 3).

Figure 2:
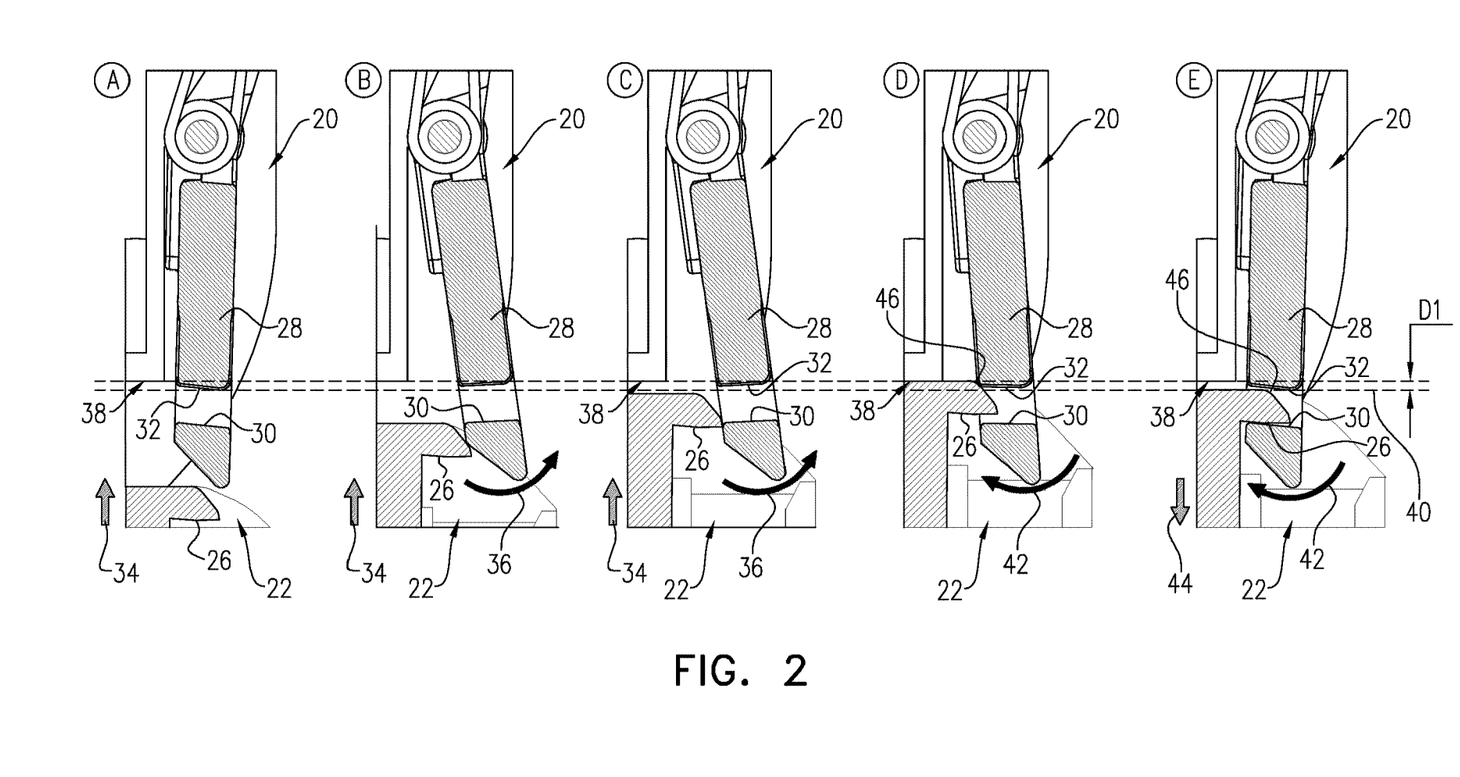
FIG. 2 is a schematic illustration showing various different positions of a latch during coupling of the tube cassette to the pump, in accordance with some applications of the present invention.

Reference is now made to FIG. 2, which is a schematic illustration showing various different positions of latch 28 during coupling of tube cassette 22 to pump 20, in accordance with some applications of the present invention. FIG. 2 shows a transition of the latch position from position (A), prior to tube cassette 22 being coupled to pump 20, through to position (E), in which tube cassette 22 is locked in the preset position with respect to pump 20.

Coupling of tube cassette 22 to pump 20 is typically done by pushing tube cassette 22 in a first direction, toward pump 20. For some applications, latches 28' and 28" may be engaged one after the other, i.e., tube cassette 22 is coupled to pump 20 by engaging one of the latches and then pivoting tube cassette 22 in a direction toward pump 20 to engage the other latch. Typically, latches 28' and 28" are identical in shape and disposed in a generally mirror-image orientation with respect to each other so it does not matter which latch is engaged first and which latch is engaged after pivoting tube cassette 22 toward pump 20. Thus, tube cassette 22 may alternatively or additionally be pushed toward pump 20 such that both latches are engaged simultaneously.

Position (A) of latch 28 represents an initial position of latch 28, prior to tube cassette 22 being coupled to pump 20. As described hereinabove, coupling of tube cassette 22 to pump 20 is via movement of tube cassette 22 in a first direction, toward pump 20. Arrow 34 represents motion of tube cassette 22 in the first direction. As tube cassette 22 moves in the first direction (e.g., due to a user pushing tube cassette 22 into pump 20), tube cassette 22 pushes latch 28 to rotate, in a first rotational direction from the initial position (A) to an angular position (B) (that is, the angular position is at a non-zero angle from the initial position). As tube cassette 22 continues to move further in the first direction, latch 28 continues its rotation in the first rotational direction until position (C) is reached, representing an open position of latch 28. Curved arrow 36 in positions (B) and (C) represents the first rotational direction in which latch 28 rotates in the transition from position (A) to position (B) and subsequently from position (B) to position (C), i.e., to the open position of latch 28.

As shown in position (C), latch 28, e.g., lower latch surface 30, has not yet engaged with locking surface 26. Typically, prior to engagement of latch 28, e.g., lower latch surface 30, with locking surface 26, in the absence of a sufficient external force maintaining the motion of tube cassette 22 in the first direction, pump 20 ejects tube cassette 22 by pushing infusion tubing 24, which in turn pushes tube cassette 22 from pump 20. If tube cassette 22 is released prior to reaching a threshold position, pump 20 will eject tube cassette 22. In order to not be ejected by pump 20, tube cassette 22 has to move, in the first direction, past the threshold position.

Thus, for some applications, pump 20 and tube cassette 22 are designed so as to allow "over-travel" of tube cassette 22 in the first direction, thus ensuring that tube cassette 22 moves past the threshold position, allowing latch 28, e.g., lower latch surface 30, to engage locking surface 26. A mechanical stop 38 is disposed within pump 20 and positioned to stop the motion of tube cassette 22 in the first direction. Thus, the external force pushing tube cassette 22 in the first direction is able to continue pushing until motion of tube cassette 22 in the first direction is stopped by mechanical stop 38. When the motion of tube cassette 22 in the first direction is stopped by mechanical stop 38, tube cassette 22 has moved past the preset position with respect to pump 20, i.e., has "over-traveled" in the first direction. The preset position with respect to pump 20 is represented by dashed line 40 in FIG. 2.

The "over-travel" position where the motion of tube cassette 22 is stopped by mechanical stop 38 is represented by position (D) in FIG. 2. As described hereinabove, latch 28, e.g., latches 28' and 28", lock tube cassette 22 in the preset position with respect to pump 20. However, until the motion of tube cassette 22 is stopped by mechanical stop 38, latch 28 allows motion of tube cassette 22 past the preset position in the first direction.

Upon engagement of latch 28, e.g., lower latch surface 30, with locking surface 26, latch 28, being typically spring-loaded, automatically moves from its open position, position (C), to a cassette-withdrawal-inhibiting position, position (D). During this transition from the open position to the cassette-withdrawal-inhibiting position, latch 28 switches direction and rotates in a second rotational direction, opposite the first rotational direction, represented by curved arrow 42 in position (D).

Typically, the cassette-withdrawal-inhibiting position of latch 28 is between the initial position of latch 28 prior to tube cassette 22 being coupled to pump 20 (position (A)) and the open position of latch 28 (position (C)), i.e., latch 28 inhibits cassette-withdrawal even before latch 28 returns to its initial position. The combination of the following three characteristics of the coupling of tube cassette 22 to pump 20 results in substantially no chance of a meta-stable coupling between tube cassette 22 and pump 20, i.e., where tube cassette 22 is coupled to pump 20 but in an unstable manner:

(a) in the absence of sufficient force to keep tube cassette 22 moving, pump 20 ejecting tube cassette 22 prior to engagement of latch 28 and locking surface 26, (b) allowing "over-travel" to ensure engagement of latch 28 and locking surface 26 as tube cassette 22 is pushed toward pump 20, and (c) latch 28 automatically moving to the cassette-withdrawal-inhibiting position (prior to latch 28 finishing closing), upon engagement of latch 28 with locking surface 26.

Subsequently to latch 28 moving to the cassette-withdrawal-inhibiting position, latch 28 locks tube cassette 22 in the preset position by pushing tube cassette 22 (further described hereinbelow) in a second direction, opposite the first direction, e.g., away from pump 20, such that tube cassette 22 moves from past the preset position to the preset position, at dashed line 40. Arrow 44 represents motion of tube cassette 22 in the second direction as tube cassette 22 is pushed by latch 28, e.g., by latches 28' and 28", back to the preset position. During this pushing of tube cassette 22 in the second direction, latch 28 continues its rotation in the second rotational direction, such that latch 28 returns to the initial position of latch 28 subsequently to the pushing of tube cassette 22 in the second direction, such as is shown in position (E) of FIG. 2.

For some applications, latch 28 pushes tube cassette 22 in the second direction via engagement between upper latch surface 32 of latch 28 and an upper locking surface 46 of tube cassette 22 (i.e., locking surface 26 is a lower locking surface 26 and tube cassette 22 is shaped to define an upper locking surface 46 as well). Subsequently to the motion of tube cassette 22 being stopped by mechanical stop 38, the external force that was maintaining the motion of tube cassette 22 in the first direction (e.g., the external force being generated by the user pushing the tube cassette into pump 20) is typically terminated. In the absence of the external force, latch 28, being typically spring-loaded, continues its rotational motion back towards the initial position of latch 28. During this continued rotational motion in the second rotational direction, upper latch surface 32 pushes upper locking surface 46 in the second direction, e.g., away from pump 20.

Typically, lower latch surface 30 and upper latch surface 32 are shaped to define the preset position of tube cassette 22, such that subsequently to latch 28 pushing tube cassette 22 into the preset position, (a) movement of tube cassette 22 in the first direction is inhibited by upper latch surface 32, and (b) movement of tube cassette 22 in the second direction is inhibited by lower latch surface 30. As used in the present application including in the claims, movement being prohibited is taken to mean that movement of larger than 20 microns is inhibited. The preset position of tube cassette 22, in turn, defines a preset distance D1 between tube cassette 22 and mechanical stop 38, and a preset distance between a pressing surface inside pump 20 (not shown) that repeatedly presses on infusion tubing 24 to deliver the fluid to the subject.

The locking of tube cassette 22 in the preset position by latch 28, e.g., latches 28' and 28", inhibits any external forces that may act on tube cassette 22 during delivery of the fluid from affecting the delivery of the fluid, by affecting the distance between the pressing surface and infusion tubing 24. For example, in the absence of latch 28 (e.g., latches 28' and 28") locking tube cassette 22 in the preset position, if an external force pushes on tube cassette 22 in the first direction, e.g., towards pump 20, the distance between the pressing surface inside pump 20 and infusion tubing 24 will decrease, which in turn may cause a bolus of fluid to be delivered to the subject and/or an inaccuracy in the volume of fluid delivered to the subject. Similarly, for example, in the absence of latch 28 (e.g., latches 28' and 28") locking tube cassette 22 in the preset position, if an external force pulls tube cassette 22 in the second direction, e.g., away from pump 20, the distance between the pressing surface and infusion tubing 24 may increase, resulting in potential under-delivery of the fluid to the subject.

Figure 3:
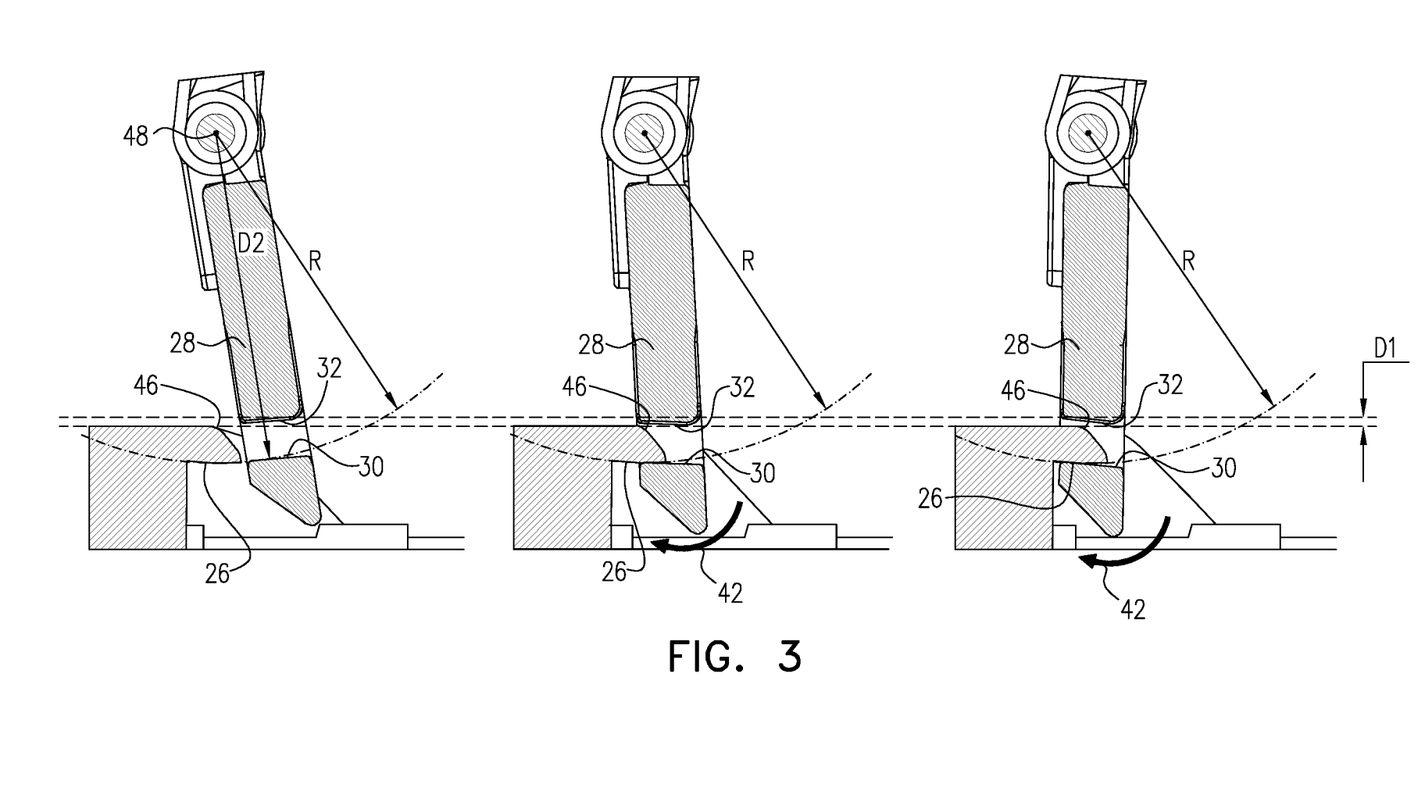
FIG. 3 is a schematic illustration showing various different positions of the latch, in accordance with some applications of the present invention.

Reference is now made to FIG. 3, which is a schematic illustration showing various different positions of latch 28, in accordance with some applications of the present invention. It is desirable that as soon as latch 28 (e.g., upper latch surface 32) has pushed tube cassette 22 into the preset position, any continued rotational movement of latch 28 in the second rotational direction (i.e., as latch 28 returns to its initial position) not change preset distance D1 between tube cassette 22 and mechanical stop 38. This is advantageous, for example, if latch 28 does not return to its initial position, tube cassette 22 is still (a) inhibited from falling out of pump 20 due to latch 28 having automatically moved to the cassette-withdrawal-inhibiting position, and (b) locked in the preset position due to latch 28 not changing the distance between tube cassette 22 and mechanical stop 38 during its rotational motion in the second direction subsequent to pushing tube cassette 22 into the preset position. (Although pump 20 is not shown in FIG. 3, distance D1 in FIG. 3 represents the same preset distance D1 shown in FIG. 2 between tube cassette 22 and mechanical stop 38 when latch 28 is in position (E).).

For some applications, this is achieved by lower locking surface 26 having radius of curvature R that is substantially equal to a distance D2 between an axis of rotation 48 of latch 28 and lower latch surface 26, such that, subsequently to upper latch surface 32 pushing tube cassette 22 into the preset position, as lower latch surface 30 continues to swing rotationally inwards towards pump 20 the motion of lower latch surface 30 follows the radius of curvature R of lower locking surface 26. Typically, the radius of curvature R being substantially equal to distance D2 ensures that as latch surface 30 continues to swing rotationally inwards, towards pump 20, a distance of typically no more than 20 microns is maintained between lower latch surface 30 and lower locking surface 26. Thus, at no point between (a) when tube cassette 22 is pushed into the preset position and (b) when latch 28 returns to the initial position, does lower latch surface 30 push on lower locking surface 26 in the first direction, e.g., toward pump 20. Yet, at substantially every point during the continued rotation in the second direction, if latch 28 were to stop its motion, lower latch surface 30 would still inhibit movement of tube cassette 22 in the second direction, as described hereinabove.

Figure 4A:
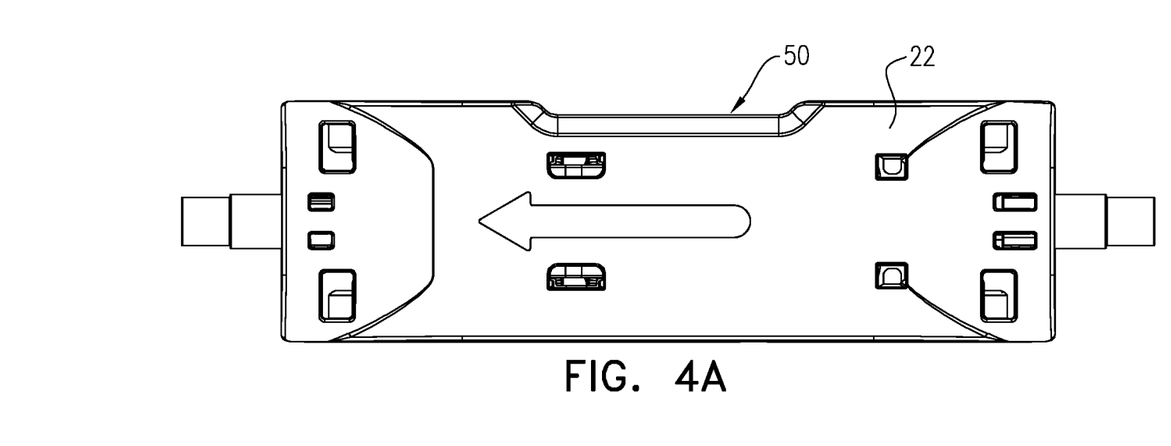
FIGS. 4A-4B are schematic illustrations of the tube cassette, in accordance with some applications of the present invention.
Figure 4B:
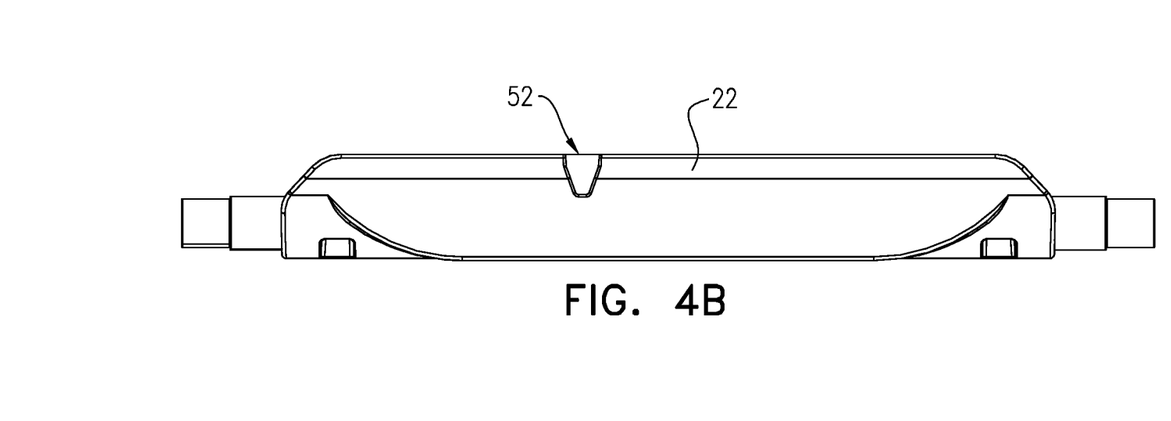

Reference is now made to FIGS. 4A and 4B, which are schematic illustration of tube cassette 22, in accordance with some applications of the present invention. For some applications, tube cassette 22 is shaped to define an orientation key to ensure that tube cassette 22 can only be inserted into pump 20 in one orientation of tube cassette 22 with respect to pump 20. For example, a first cavity 50 in tube cassette 22 may engage with a corresponding protrusion on pump 20 (or vice versa) such that if a user tried to insert tube cassette 22 into pump 20 in a different orientation, the protrusion on pump 20 would inhibit the insertion. For some applications, a side-to-side positioning key ensures that once tube cassette 22 is locked in the preset position with respect to pump 20, not only is the distance between the pressing surface inside pump 20 and infusion tubing 24 tightly defined, but also the longitudinal site along infusion tubing 24 at which the pressing surface presses on infusion tubing 24. For example, a second cavity 52 in tube cassette 22 may engage with a corresponding protrusion on pump 20 (or vice versa) to ensure that tube cassette 22 cannot move from side-to-side with respect to pump 20 when tube cassette 22 is coupled to pump 20.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for delivering a fluid to a subject through infusion tubing, the apparatus comprising:
    (A) a tube cassette configured to receive the infusion tubing, the tube cassette shaped to define a locking surface;
    (B) a pump comprising a latch,
        (i) the tube cassette being configured to be removably coupled to the pump, and
        (ii) the latch being configured to (a) engage with the locking surface and (b) lock the tube cassette in a preset position with respect to the pump when the tube cassette is coupled to the pump; and
    (C) a mechanical stop disposed within the pump,
        (i) the mechanical stop being positioned to stop motion of the tube cassette in a first direction, such that when the motion of the tube cassette in the first direction is stopped by the mechanical stop, the tube cassette has moved past the preset position in the first direction, and
        (ii) the latch being configured to:
            (a) until the motion of the tube cassette is stopped by the mechanical stop, allow motion of the tube cassette past the preset position in the first direction,
            (b) automatically move from an open position to a cassette-withdrawal-inhibiting position upon engagement of the latch with the locking surface, and (c) subsequently, lock the tube cassette in the preset position by pushing the tube cassette in a second direction opposite the first direction, from past the preset position to the preset position.

2. The apparatus according to claim 1, wherein the latch is a spring-loaded latch.

3. The apparatus according to claim 1, wherein the latch is configured to, during the coupling of the tube cassette to the pump, sequentially:
   (a) rotate in a first rotational direction during a transition from (i) an initial position prior to the tube cassette being coupled to the pump to (ii) the open position, during motion of the tube cassette in the first direction,
   (b) rotate in a second rotational direction, opposite the first rotational direction, in the transition from (i) the open position to (ii) the cassette-withdrawal-inhibiting position, and
   (c) continue rotation in the second rotational direction during the pushing of the tube cassette in the second direction from past the preset position to the preset position, such that the latch returns to the initial position subsequently to the pushing of the tube cassette in the second direction.

4. The apparatus according to claim 1, wherein the cassette-withdrawal-inhibiting position of the latch is between (a) an initial position of the latch prior to the tube cassette being coupled to the pump and (b) the open position.

5. The apparatus according to claim 1, wherein the pump and the tube cassette are configured such that, in the absence of a sufficient external force maintaining the motion of the tube cassette in the first direction prior to the engagement of the latch with the locking surface, the pump is configured to eject the tube cassette by pushing the infusion tubing which in turn pushes the tube cassette from the pump.

6. The apparatus according to claim 1, wherein the latch comprises a lower latch surface, the lower latch surface being configured to engage with the locking surface of the tube cassette, the lower locking surface having a radius of curvature that is substantially equal to a distance between an axis of rotation of the latch and the lower latch surface.

7. The apparatus according to claim 1, wherein:
   the locking surface is a lower locking surface, and the tube cassette is further shaped to define an upper locking surface, opposite the lower locking surface, and
   the latch comprises a lower latch surface and an upper latch surface, (a) the lower latch surface being configured to engage with the lower locking surface, and (b) the upper latch surface being configured to engage with the upper locking surface when the tube cassette is coupled to the pump, such that:
   (i) engagement between the lower latch surface and the lower locking surface inhibits cassette withdrawal when the latch moves from the open position to the cassette-withdrawal-inhibiting position, and
   (ii) subsequently, the upper latch surface pushes the tube cassette in the second direction by pushing on the upper locking surface of the tube cassette.

8. The apparatus according to claim 7, wherein the lower and upper latch surfaces are shaped to define the preset position of the tube cassette, such that subsequently to the upper latch surface pushing the tube cassette in the second direction, (a) movement of the tube cassette in the first direction is inhibited by the upper latch surface, and (b) movement of the tube cassette in the second direction is inhibited by the lower latch surface.

9. The apparatus according to claim 7, wherein the lower locking surface is shaped to define a radius of curvature that is substantially equal to a distance between an axis of rotation of the latch and the lower latch surface.

10. The apparatus according to claim 1, wherein:
    the locking surface is a first locking surface and the tube cassette is shaped to define a second locking surface, and
    the latch is a first latch and the pump further comprises a second latch, the second latch being configured to (a) lockingly engage with the second locking surface and (b) lock the tube cassette in the preset position with respect to the pump when the tube cassette is coupled to the pump.

11. The apparatus according to claim 10, wherein the first and second latches are disposed on opposite sides of the pump.

* * * * *